US008440986B2

(12) United States Patent
Gofron et al.

(10) Patent No.: US 8,440,986 B2
(45) Date of Patent: May 14, 2013

(54) ON AXIS SAMPLE VISUALIZATION ALONG A SYNCHRONTRON PHOTO BEAM

(75) Inventors: Kazimierz Gofron, Plainfield, IL (US); Michael Molitsky, Plainfield, IL (US)

(73) Assignee: UChicago Argonne, LLC., Chicago, IL (US)

( * ) Notice: Subject to any disclaimer, the term of this patent is extended or adjusted under 35 U.S.C. 154(b) by 303 days.

(21) Appl. No.: 12/766,275

(22) Filed: Apr. 23, 2010

(65) Prior Publication Data

US 2011/0260064 A1   Oct. 27, 2011

(51) Int. Cl.
*G01N 21/64* (2006.01)

(52) U.S. Cl.
USPC ........................................ 250/461.1; 378/205

(58) Field of Classification Search ............... 250/461.1; 378/73–81, 205
See application file for complete search history.

(56) References Cited

U.S. PATENT DOCUMENTS

| | | | |
|---|---|---|---|
| 6,256,143 B1 * | 7/2001 | Knight et al. | 359/376 |
| 6,444,968 B1 * | 9/2002 | Burt et al. | 250/208.1 |
| 6,658,864 B2 * | 12/2003 | Thomas et al. | 62/63 |
| 6,853,703 B2 * | 2/2005 | Svatos et al. | 378/65 |
| 7,672,430 B2 * | 3/2010 | Chapman et al. | 378/71 |
| 2005/0043597 A1 * | 2/2005 | Xie | 600/315 |
| 2005/0237522 A1 * | 10/2005 | Swift et al. | 356/317 |

FOREIGN PATENT DOCUMENTS

| | | | |
|---|---|---|---|
| FR | 2650438 | * | 2/1991 |
| JP | 06011465 | * | 1/1994 |

OTHER PUBLICATIONS

Owen et al. "A new on-axis multimode spectrometer for the macromolecular crystallography beamlines of the Swiss Light Source" J. Synchrotron Radiation 16, 173-182, (2009).*

* cited by examiner

*Primary Examiner* — David Porta
*Assistant Examiner* — Edwin Gunberg
(74) *Attorney, Agent, or Firm* — Cherskov Flaynik & Gurda, LLC.

(57) ABSTRACT

The present invention provides a method for on-axis visualization of a target placed in a photon beam, the method comprising: placing the target in the path of the photon beam; selecting a mirror with an external reflecting surface; placing the mirror on a mirror support so that the surface faces the target; placing a reflective microscope so as to collect photons emanating from the target that have been reflected by said surface; counting and analyzing photons collected by the microscope with a CCD camera; and storing and analyzing data collected by the camera.

19 Claims, 5 Drawing Sheets

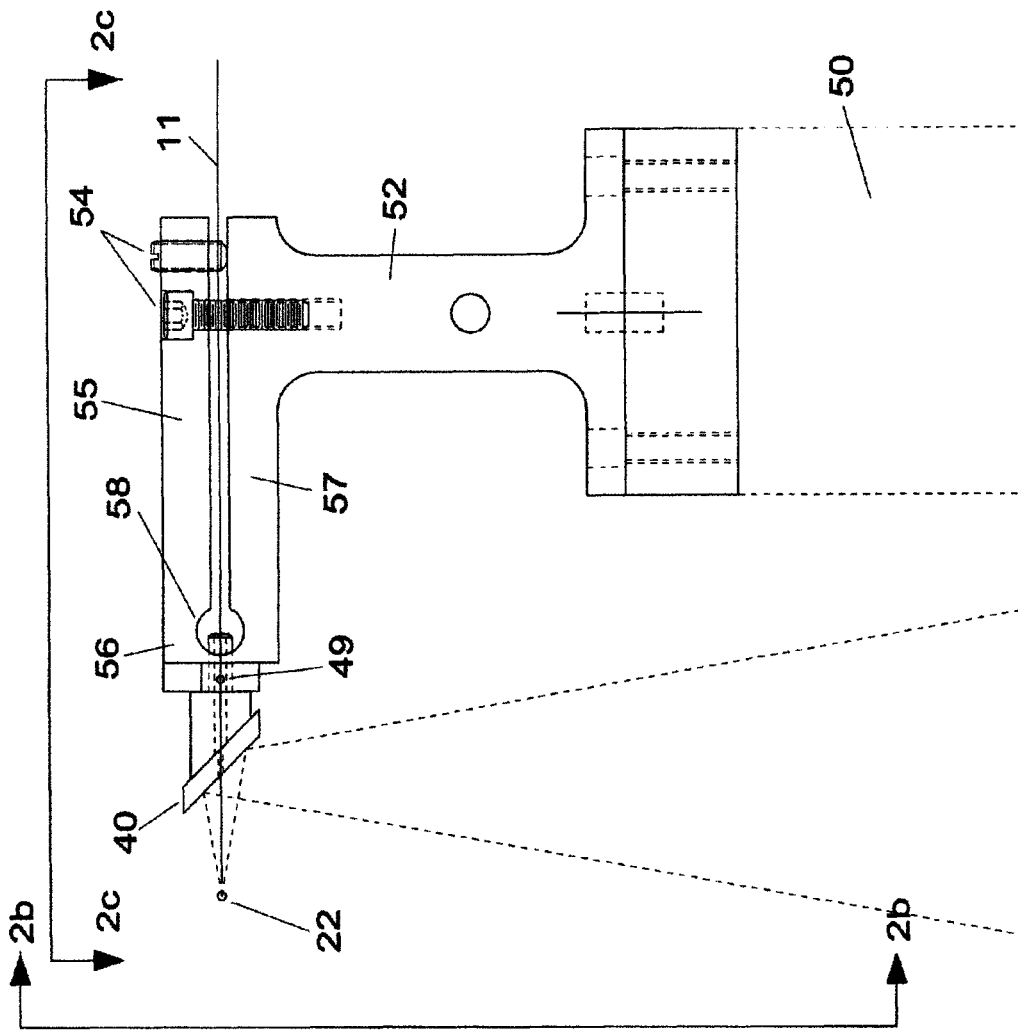
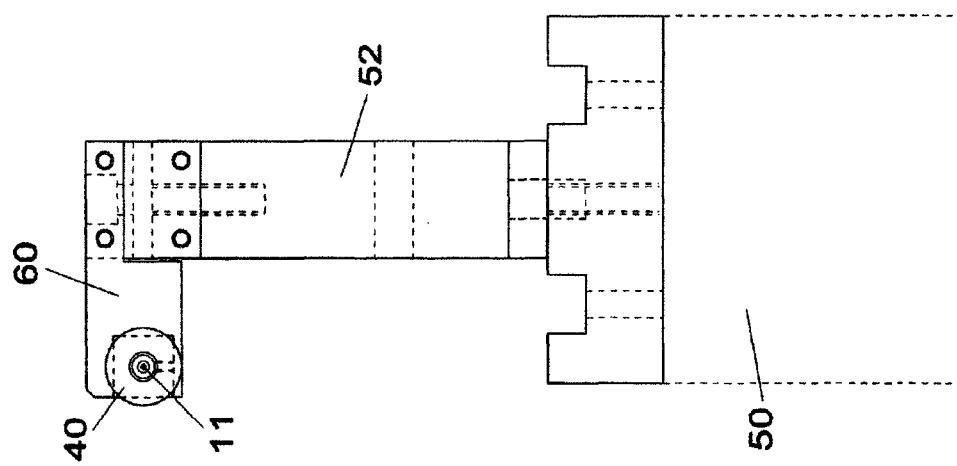
Fig. 2a
Fig. 2b

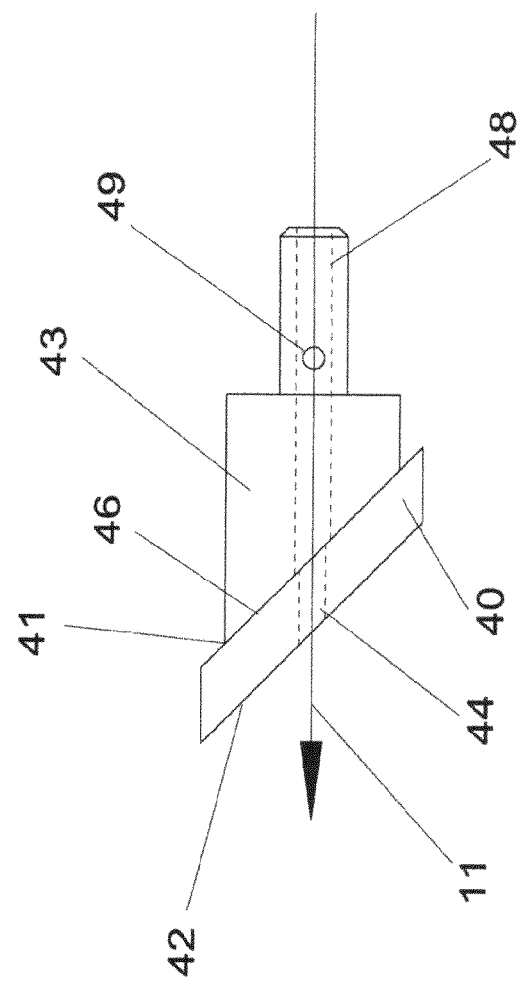

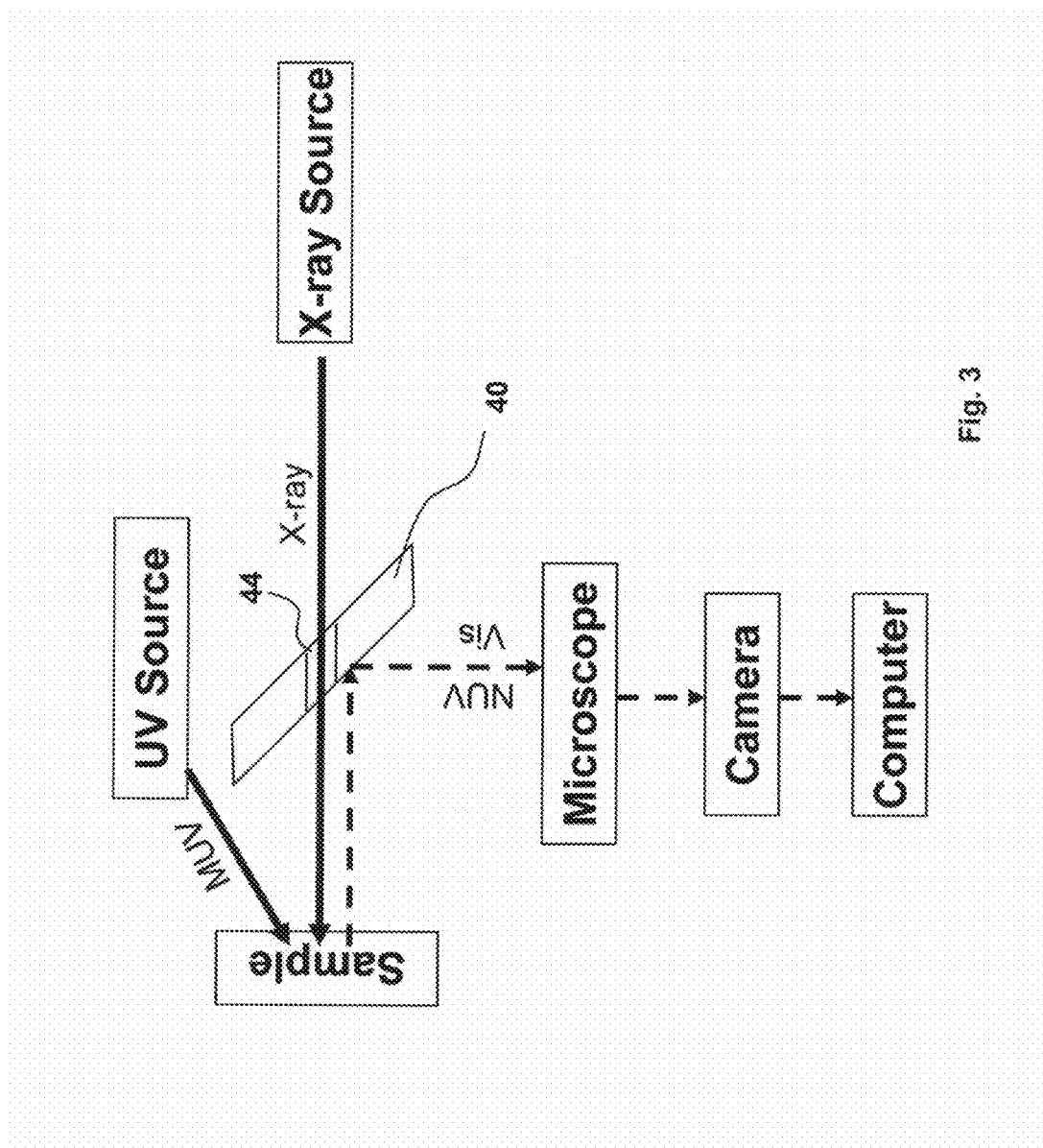

ON AXIS SAMPLE VISUALIZATION ALONG A SYNCHRONTRON PHOTO BEAM

BACKGROUND OF THE INVENTION

1. Field of the Invention

This invention relates to the study of materials using high energy photons and, more particularly, this invention relates to an on-axis method for studying samples using synchrotron-produced x-rays.

2. Background of the Invention

Macromolecular crystallography involves the study of crystal structure of target materials by observing how those structures diffract and otherwise affect incident electromagnetic radiation. These studies are optimized by accurate placement of the target crystal in the line of travel of the radiation.

High-throughput data collection for macromolecular crystallography requires an automated sample mounting and alignment system for crystals that functions reliably when integrated into protein-crystallography beamlines at synchrotrons. Rapid mounting and dismounting of the samples increases the efficiency of the crystal screening and data collection processes, where many crystals can be tested for the quality of diffraction.

A key factor for high performance X-ray protein crystallography beam lines is the overall duty cycle of the beam line including efficient optics alignment, automation of sample handling, crystal visualization and alignment, data collection and data analysis. Many synchrotron radiation facilities are now concentrating on these high-throughput projects, which will have an enormous influence on the overall throughput of the field.

Indirect Image Technologies

It is normally assumed that sample visualization cannot be done during data collection along the x-ray beam without degradation of the image quality, in conjunction with "kappa geometry" (i.e rotation of a sample around three independent axes) and in the presence of a cold stream such as boiled-off gas from liquid nitrogen or liquid helium. Heretofore, these processes required a microscope with a long working distance also having an optical magnification of about 10×. Also the presence of a beam passage bore in the optics degrades the image because paraxial rays are lost.

On-axis visualization can be done with removable optical components prior to (or after) data collection by swinging a microscope in place. The microscope is used initially to align the crystal. Afterwards, the components of the microscope are retracted from the on-axis area near the sample. Data collection in this configuration relies on stability of the goniostat supporting the sample, stability of the x-ray beam, and precision of the initial alignment. This beam visualization method has a major limitation in that visualization is not done during data collection. Moreover, these machinations require precise maneuvering, and therefore high mechanical stability Off axis, or "indirect alignment" visualization methods rely on visualization techniques based on microscopes with fixed optical components. However, off axis alignment suffers from parallax error which results in inferior precision of alignment. The best practice with off axis alignment requires two cameras with orthogonal views of the sample.

Typical indirect crystal centering methods comprise two steps. In this method, the visible light cameras are mounted and moving with goniostat support (support of omega, kappa, and sample motions, see #58 infra). First the center of omega rotation of the goniostat is determined by using well defined pointy object (such as AFM cantilever), a fiducially marked cross-hair is then placed at the center of omega rotation in video stream from cameras. Second, the location of the x-ray beam is determined by having the beam strike a phosphor screen; placed at omega center of rotation; a goniostat support is moved so that the fiducially marked cross-hair is at the beam location. Finally, with the help of a visible light microscope, the target crystal is placed manually in the center of omega rotation and at the cross-hairs. Visible illumination is typically done from the side or behind the crystal (bright field illumination).

Other approaches include using high power broadband sources and filtered out UV component to excite the visible fluorescence. Drawbacks to this approach include the need for a large UV source system, and a lack of understanding of the physics involved.

Still others have used pulsed UV (266 nm) lasers. However, such pulsed lasers induce crystal damage due to adiabatic processes. Also, these systems use visible spectrum for imaging with visible light cameras.

Direct Visualization Technologies

On-axis observation of crystals allows visualization of x-ray beams without parallax distortion and visualization of the crystal from the x-ray beam point of view. Sample alignment with on-axis visualization compares favorably to prior (non-axial) alignment techniques which generally suffer from parallax errors. Misjudgments of fluorescence depth from phosphor illumination at various photon energies can be one of the reasons for misalignment. On-axis visualization allows alignment verification during data collection.

All of the aforementioned off-axis techniques fail to readily locate a biological crystal in the sample holder so as to place it in the center of the x-ray beam. Macromolecular Crystallography at third-generation synchrotrons has been relying primarily on light in the visible spectrum (400 nm-600 nm wavelength) for sample alignment, with optical microscopes being used to achieve sample alignment.

The main motivation for the use of crystal visualization microscopy at the synchrotron beamline is to achieve precise placement of a small biological crystal in the same x-ray beam that is used for measurement of the sample properties. The typical 10 μm-50 μm size biological crystal must be placed at the center of the experimental apparatus, and the sample must be able to rotate around its axis and around the beam axis. Moreover, the x-ray beam center should pass through the center of rotation of the apparatus and through the crystal center. For optimal x-ray diffraction by the sample crystal, a uniform intensity x-ray beam should match the size of the crystal. The typical x-ray beam heretofore used has had a 25-75 μm rectangular cross-section.

The few successful on-axis sample visualization systems in use are devices with line-of-sight view along x-ray beam (from source direction) and without parallax errors ("direct alignment") visualization. The MD2 diffractometer (Maatel) has on-axis visualization with a compound objective lens (with as many as 10 component lenses) placed very close to the sample (one inch or so) followed by a 45° mirror and finally a camera. The objective lens has a bore drilled through it to allow unobstructed passage of x-rays through the lens. The system introduced by Owens et al. (J. Synchrotron Rad. 16, 173-182 (2009)) utilizes a reflecting telescope with an objective in close proximity to the sample (approximately an inch) a 45° mirror between the objective and the primary mirror and finally a camera. A bore is required through the objective and the 45° mirror to allow passage of the beam.

The disadvantage of current on-axis visualization systems is that paraxial rays that could be used in image formation are lost in the bore drilled through objective and 45° mirror optics. This loss of image-forming paraxial rays results in inferior image quality at the center of the microscope. Also, lenses introduce chromatic aberration (different focal length for different wavelengths) making such a system unsuitable for work spanning a wide range of wavelengths with high image quality at the center needed for beam and sample visualization. The close proximity between the objective and the sample introduces spherical aberration. Moreover, alignment of the apparatus is critical in that one must ensure that the x-ray beam does not impact the walls of the bore through which it passes. Finally the lack of adequate working space near the sample limits the experiments that can be performed. Specifically, one cannot perform the full complement of sample rotations that are necessary for a complete determination of a sample.

A need exists in the art for a sample visualization system that pinpoints location of the sample relative to the radiation beam used to illuminate the sample. The system should also facilitate sample visualization during data gathering. The system should expedite alignment of the sample to enhance streamlining of such processes.

SUMMARY OF THE INVENTION

An object of this invention is to provide a method and an apparatus for on-axis visualization of samples in a photon beam during data gathering that overcome many of the disadvantages in the prior art.

Another object of the present invention is providing a direct method of crystal centering and visualization. A feature of the direct method is excitation of molecules near UV fluorescence that is imaged by cameras. The advantage of this method is that it verifies location of the crystal with respect of the synchrotron x-ray beam. It also locates/finds the crystal with respect to the apparatus.

Still another object of the present invention is providing an indirect method of crystal centering and visualization. A feature of the indirect method is the UV excitation and deexcitation of crystals using a UV source instead of the x-ray source used in the direct method, mentioned supra. An advantage of the invention is that the deexcitation UV fluorescence allows imaging and finding of the biological crystal, including finding the size, shape, and center of the optical mass of the crystal. This information will be utilized in positioning the center of mass of the crystal in line with an imaging x-ray beam.

Another object of this invention is to provide a method and an apparatus for on-axis visualization of samples placed in a photon beam that provides high quality optics with ample working room around the sample. A feature of this invention is the use of a reflecting microscope. An advantage of this invention is that it allows placement of the objective at about 15 cm or farther from the sample. An advantage of the invention is that this working distance facilitates manipulation of the sample while leaving the visualization equipment in place, without loss of image-forming rays. Another advantage of this invention is the elimination of chromatic aberration for rays at different wavelengths.

Yet another object of the present invention is to provide a method and apparatus for on-axis visualization of samples which simplifies sample visualization and beam alignment. A feature of the invention is the use of non-dispersive optics. An advantage of the invention is that it has negligible chromatic aberration.

In brief, the present invention provides a method for on-axis visualization of a target placed in a photon beam, said method comprising: placing the target in the path of the photon beam; selecting a mirror with an external reflecting surface; placing said mirror on a mirror support so that said surface faces said target; placing a reflective microscope so as to collect photons emanating from said target that have been reflected by said surface; counting and analyzing photons collected by said microscope with a camera, a CCD or ECCD camera where indicated; and storing and analyzing data collected by the camera.

For x-ray diffraction work, the invented method comprises boring a passage through the mirror at about a 45 degree angle to said reflecting surface and placing said mirror so that said photon beam traverses said mirror through said passage before said beam strikes said crystal.

Also, the present invention introduces an apparatus for on-axis visualization of a target placed in a photon beam, said apparatus comprising: a target support 23 for holding the target in the path of the photon beam; a mirror with an external reflecting surface and with a passage bored through the mirror at about a 45 degree angle to said reflecting surface; a mirror support holding said mirror so that said surface faces said crystal and so that said photon beam traverses said mirror through said passage before said beam strikes said crystal; a reflective microscope placed so as to collect photons emanating from said crystal that have been reflected by said mirror; a camera for counting and analyzing photons collected by said microscope; and a computer for storing and analyzing data collected by the camera.

BRIEF DESCRIPTION OF THE DRAWING

The foregoing and other objects, aspects, and advantages of this invention will be better understood from the following detailed description of the preferred embodiments of the invention with reference to the drawing, in which:

FIG. 2a is a front view taken along the line 2a-2a of FIG. 2b of a mount for a 45 degrees mirror, in accordance with features of the present invention;

FIG. 2b is a side view of a mount for a 45 degrees mirror, in accordance with features of the present invention;

FIG. 2d is a detail view of a holder for a 45 degrees mirror, in accordance with features of the present invention; and FIG. 3 is a block diagram showing the experimental arrangement for on-axis x-ray localization simultaneously with visualization by means of UV and visible fluorescence radiation, in accordance with features of the present invention.

DETAILED DESCRIPTION OF THE INVENTION

Figure 1:
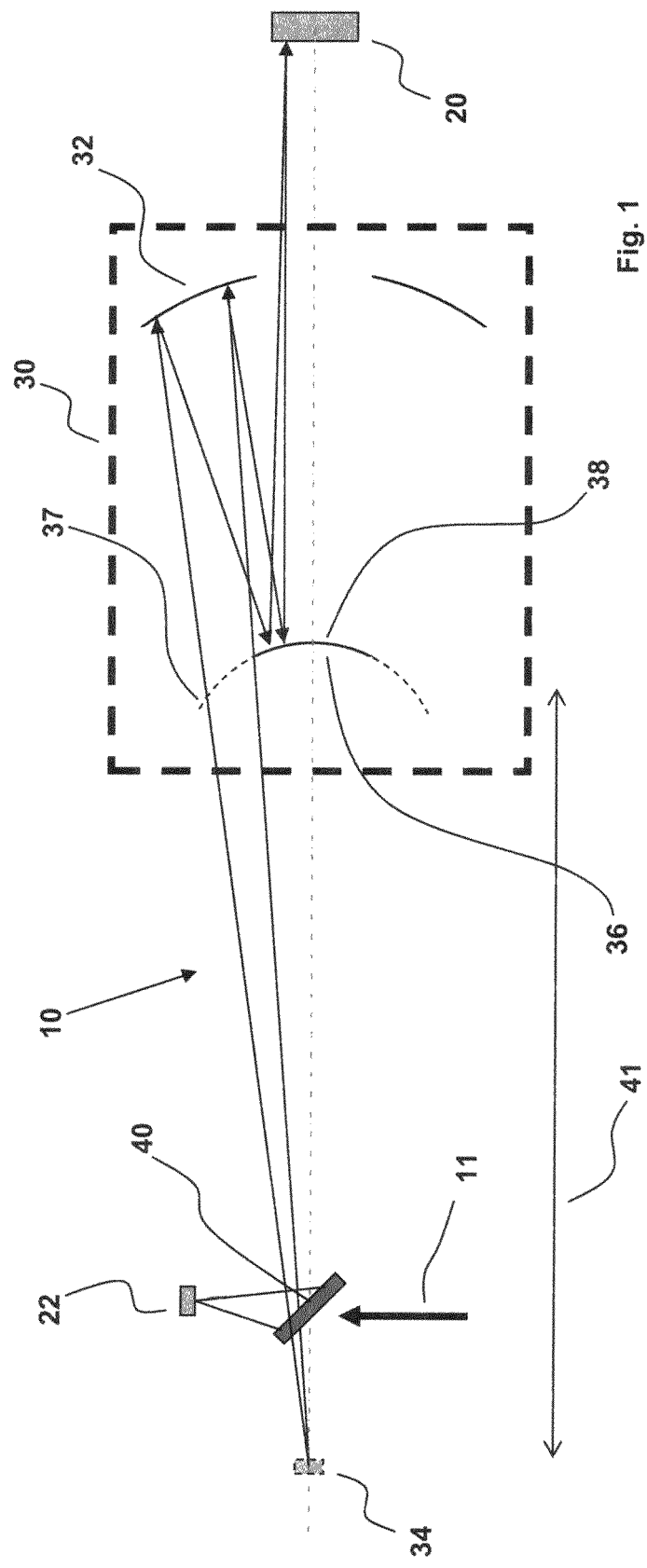
FIG. 1 is an overall view of an exemplary embodiment of an apparatus for on-axis visualization for a sample in an x-ray beam, in accordance with features of the present invention.

The foregoing summary, as well as the following detailed description of certain embodiments of the present invention, will be better understood when read in conjunction with the appended drawings.

As used herein, an element or step recited in the singular and preceded with the word "a" or "an" should be understood as not excluding plural said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising" or "having" an element or a plurality of elements having a particular property may include additional such elements not having that property.

The present invention utilizes an on-axis system for beam and sample visualization. This on-axis sample visualization method can be used in the infra-red, visible, UV, and x-ray portions of the electromagnetic (EM) spectrum. For illustrative purposes only, this specification will address x-ray visualization.

The invented on-axis visualization solution exploits the fact that paraxial rays are not used in image forming for some reflective optics designs. Exploiting that property, a bore drilled or otherwise formed in a 45° mirror allows unobstructed transmission of x-rays in that unused paraxial space.

On-axis visualization is a significant improvement over other existing on-axis designs and off-axis designs because it allows simultaneous beam and sample visualization during data collection, without image degradation, and works with all necessary existing instruments. The on-axis solution demonstrated here allows x-ray beam visualization and biological crystal visualization during data collection, with high special resolution, from the x-ray source viewpoint, without image degradation, and with long working distance.

This on-axis solution has no degradation of image quality on optical axis despite the use of a fairly large bore in the 45° mirror for x-ray transport. The parameters of the 45° mirror are determined as a function of the working distance, sample size, and sample to mirror distance. The on-axis (along x-ray beam view) visualization simplifies sample and x-ray beam alignment, and eliminates parallax error. Beam centering is significantly easier using on-axis visualization.

An actual x-ray diffraction experiment consists of rotating the crystal (at a constant angular speed) in the x-ray beam, and collecting diffraction images for each one degree rotation (total of about 180 degrees covered). For this rotation, crystals larger than 30 microns should be aligned within ±5 microns of the x-ray beam.

On-axis visualization using Maksutov-Cassagrain optics or any similar objective optics will work for many sample imagings. Among alternative objective designs that could be used is a Newtonian reflector, and a Schmidt-Cassegrain configuration. There are many possible applications of on-axis visualization, not limited to synchrotron x-ray beam visualization. One may use this design for visualization in many applications. For luminescence imaging, the excitation wavelength should be at one of the absorption maxima (e.g., 280 nm, or ~220 nm in the case of aromatic rings present in the biological sample). Illumination imaging such as visible light imaging is done by using visible light illumination and observing light of the same wavelength. The visible and/or UV sources could be strobed (pulsed) to overlay the images.

Visualization capabilities are often influenced by the microscope and the camera used. For example, the Questar QM100 optics model used in the invention was purchased with UV coatings (UV Enhanced Aluminum: >85%250-600 nm) and UV-transparent lenses (UV Fused Silica: 200-2000 nm). The 45° mirror was purchased from Edmund Optical and has a similar UV enhanced coating that reflects in the UV and visible ranges. While several CCD cameras are suitable for visualization determinations, the inventors used the aforementioned Andor cameras for x-rays and for UV.

The invented system accommodates sample crystal sizes ranging from a few microns to a hundred microns. The optical magnification of macromolecular crystallography alignment optical microscopes preferably is about 10. In one embodiment of the system, resolution of the optical microscopes is about one micron. This will facilitate the identification of biological crystals.

Preferably, the working distance of crystal alignment microscopes is at least 3 inches and most preferably at least 5 inches. The long working distance requirement originates from the presence of a cold stream (biological crystals are kept typically near liquid $N_2$ temperature). In addition, a minimum of approximately a half an inch is required around the sample for unobstructed robot arm access for crystal mounting and dismounting. Empirical studies will determine further access requirements. As shown in FIG. 1, the on-axis optical system, designated as numeral 10-comprises three major components: a camera 20, an objective microscope 30, and a 45° mirror 40. An exemplary camera is the Hitachi HV-C20 CCD. However, other cameras are also suitable. One may use a light image intensifier in conjunction with the camera.

The on-axis reflective microscope 30 is a Maksutov-Cassegrain microscope. Such microscopes are commercially available, for example, as the Questar QM100. Generally, the microscope 30 contains a plurality of mirrors. A first mirror, 32 determined to be the "Primary" mirror is the first reflective surface to receive the sample image 34 emanating from the sample 22 irradiated by the x-ray beam 11.

A second mirror 36 referred to as the front or "secondary" mirror comprises a reflective film 38 deposited on the convex side of a very thin arcuate lens 37.

The 45° flat mirror 40 was purchased from Edmund Optics. A transverse bore is subsequently drilled or otherwise formed through approximately the center of the mirror and substantially along a 45 degree angle relative to the reflecting surface 42 of the mirror. Diamond and/or ultrasound drilling is a suitable means for effecting the bore. Preferably, the bore exceeds the cross-section of the synchrotron beam. The 45° flat mirror reflects externally (i.e. the reflected photons do not penetrate inside the mirror glass) and has elliptic outer dimensions so as to appear to be a circle when viewed along the beam direction. The mirror coatings are selected so that UV reflectivity is enhanced to allow observation of the many important physics phenomena in biological materials that occur in the UV part of the spectrum.

The working distance W 41 is primarily governed by the capabilities of the objective lens of the QM100. Similarly, the resolution of 1.1 µm for QM100 is limited by the Numerical Aperture, which for QM100 is 0.11. The field of view is currently limited by the size of the CCD chip in the camera, and not by the objective. The microscope magnification is fixed (no automatic zoom) for the sake of stability.

The use of reflective optics instead of refractive optics provides simplicity in design; eliminates chromatic aberration: when reflective optics focuses at one wavelength (e.g. 200 nm) it also focuses at all other wavelengths (e.g. 200 nm to 500 nm and beyond); and eliminates paraxial rays (rays in the center cone) when forming images. These paraxial rays are blocked by the secondary mirror. Thus, in that excluded region (containing rays not used for image formation), a bore can be drilled in that portion of the 45° mirror 40 intersecting the beam without degrading image quality. This combination of long working distance, resolution, light throughput, large f-number, depth of field, and compactness leads to the choice of a Maksutov-Cassegrain design.

The QM100 reflective microscope consists primarily of two spherically curved mirror surfaces: the primary mirror 32 and a secondary mirror 36. The Working Distance W is measured as the distance from sample to the entrance of the QM100 optics. For the present arrangement, W=15 cm. At optics ingress near the secondary mirror 36, the perceived size of the secondary mirror 36 is defined as inner diameter (ID), and the perceived size of the primary mirror 32 is defined as outer diameter (OD). ID, OD, x, and W determine the parameters of the 45° mirror. The point 'S' is the perceived sample location 34 due to the use of mirror 40, and "Sample" designates the sample's actual location 22.

For a point sample, the maximum inner and minimum outer diameters of the elliptically shaped 45° mirror as viewed from sample position are:

$$PmID = \frac{x}{W} * ID \quad (1)$$

$$PmOD = \frac{x}{W} * OD \quad (2)$$

Where PmID is point sample mirror inner diameter bore, and PmOD is the point sample mirror outer diameter.

However, the typical sample has extended size, and for transverse size s of the sample, the formulas are modified to:

$$EmID = \frac{(x - c1)}{(W - c1)} * ID \text{ where } c1 = \frac{(W * s)}{(ID + s)} \quad (3)$$

$$EmOD = \frac{(x + C2)}{(W + C2)} * OD \text{ where } C2 = \frac{(W * s)}{(OD - s)} \quad (4)$$

The EmID is Extended Sample Mirror Inner Diameter, and EmOD is Extended Sample Mirror Outer Diameter. The c1 and C2 are corrections for Field of view or effective transverse size of the sample.

Specifically, with QM100 optics and Hitachi HV-C20 camera, W=171 mm, s=0.7 mm, x=21 mm. These result in maximum mirror inner diameter bore EmID=2.16 mm, the minimum mirror outer diameter EmOD=7.81 mm. It is preferable that the 45° mirror not be closer to the sample than 5 mm for the dimensions chosen, or the image quality will be degraded due to loss in the bore of image-forming light rays.

Flat Mirror Detail

In order to facilitate alignment of the x-ray beam, flat elliptically-shaped mirrors are utilized. These are commercially available from such supply houses as Edmund Optics. A variety of sizes are appropriate, for example, Edmund part number=NT43-573, defines a 0.5 in minor diameter.

As shown in FIG. 2*d* an embodiment of the invention defines a transverse extending bore 44 with an inner diameter of about 1.6 mm at 45° with respect to the mirror surface 42. The mirror bore is large enough to pass the x-ray beam without much alignment difficulty, and has 0.5 mm guard for alignment adjustment. An opposite facing (i.e. downstream facing) surface 46 of the mirror is ground away or otherwise adapted to receive the mirror holder 43. The 45° mirror has a glue joint 41 to a mounting block 43 as shown in FIG. 2*d*. The mounting block has a bore 48 aligned with that of the mirror and small side opening 49 which allows helium gas access to the x-ray path for scattering reduction.

The 45° mirror reflects at the front or forward-facing surface 42. Internal reflection from inside a prism or from the back surface mirrors was not used because as light traverses glass material, it would be shadowed by the bore drilled through the mirror center glass, possibly removing image forming rays. The surface quality parameters of the mirror were determined using a MicroXAM RTS surface profiler with objective lens 5×. Local deviations in the surface were found to be less then 1.2 nm RMS, and the maximum peak to valley ratio ("PV") less than 35 nm, with the radius of curvature of the whole mirror larger then 30 *m*.

The sample and mirror mountings facilitate rotation of the sample around three axes that intersect at the sample center of mass. A first axis ("x axis") at the end of which the sample is held is perpendicular to the beam ("z axis"). Conventionally a rotation around the x axis is designated as an β rotation. The second rotation ("κ rotation") is around a second axis β in a plane perpendicular to the beam and at an angle α with respect to the z axis. The angle α is chosen between 50 and 60 degrees. Finally one rotates the crystal around the new position of the x axis (φ rotation) The ω, κ, and φ rotations are equivalent to a set of Euler angles rotations.

One designates as "Kappa geometry" the arrangement which allows the latter additional rotational motions of the sample—which is preferable for single crystal work. However additional motion comes at the price of less physical space available near sample, which requires that the first optical element of the microscope be far away so as to allow the motion of the sample as that of the hardware used to carry out the rotations. The "long working distance" (WD) optics, needed with Kappa geometry is preferably at least 15 cm (6 inches). At the same time, optical magnification of the microscope preferably is about 10×—and this combination is what severely limits the available choices. Several vendors sell kappa goniometers, e.g. Brucker and Huber kappa. Huber is best if one requires two rotation arms.

Figure 2C:
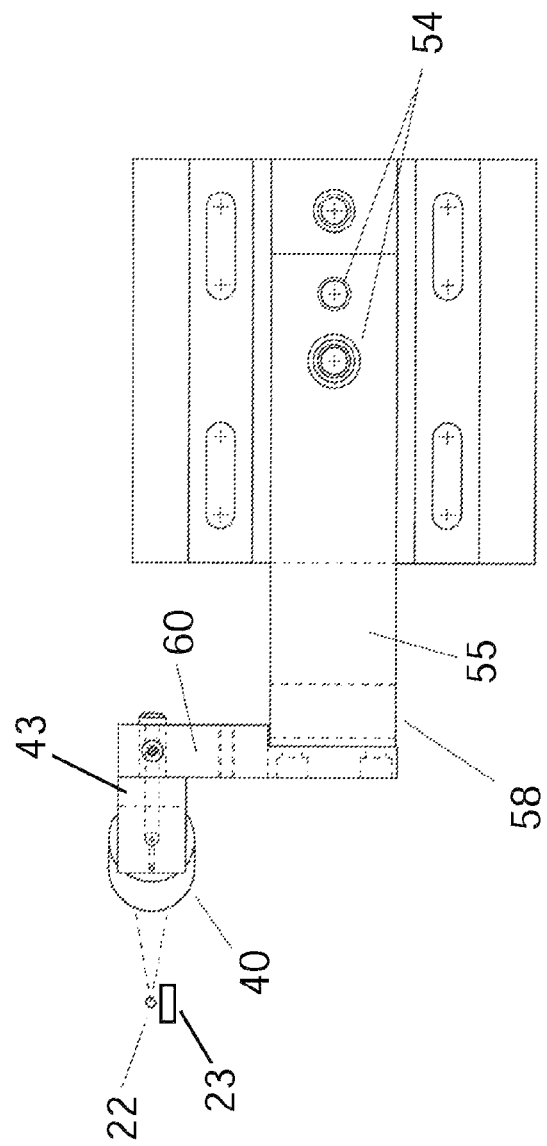
FIG. 2c is a top view taken along the line 2c-2c of FIG. 2b of a mount for a 45 degree mirror, in accordance with features of the present invention.

For on-axis viewing, the 45° mirror requires an adjustable mount. The mount is illustrated in FIGS. 2*a*-2*d*. FIG. 2*b* is a front view taken along the line 2*b*-2*b* of FIG. 2*a*. FIG. 2*a* is a-side view of the mount; FIG. 2*c* is a top view of the mount taken along the line 2*c*-2*c* of FIG. 2*b*; and FIG. 2*d* is a detail view of the mount. The mount is mounted on a Thor-Labs stage 50 and comprises a column 52 from which extends a U-shaped arm 55, with the arc in the U forming a compliant hinge 58. The separation between the two sections 56, 57 is adjusted by means of the two adjustment screws 54. The mirror holder 43 is mounted on a member 60 that extends from the arm 55. (See FIG. 2*c*)

The requirements are that the bore be on the same optical axis as the microscope objective, and "point" at the sample single crystal (such that the image of the crystal should be in center of the image picture). Particularly challenging adjustments are tilting of the mirror. For these maneuvers, a weak link adjuster is utilized. This allows tiny tilt adjustments of the mirror by adjusting two screws. The left right adjustment is done by rotating a mirror mounting plate about the optical axis of the microscope objective motions of an xyz stage (e.g. Thorlabs MBT602, Thorlabs, Newton, N.J.) to which the mirror is mounted.

There are significant advantages conferred by the invented system:

1. X-Ray Beam Visualization:

Improved spatial location of the x-ray beam, as well as determinations of its dimensions and intensity, is significantly facilitated by on-axis viewing. For instance, parallax error is eliminated when viewing along the beam direction, with the 3D nature of x-ray fluorescence being less relevant. Synchrotron beam visualization determines size and shape of the x-ray beam. The x-ray beam is viewed as it impacts a phosphor screen. The 3D nature of x-ray fluorescence makes off-axis visualization quite difficult for studies of the beam properties at the sample position.

2. Biological Crystal Visualization

The on-axis images of biological crystals are very clear, and resolution and image quality is excellent throughout the image. The center of the image does not suffer the degradation of image quality which is often observed in on-axis designs that use refractive optics.

3. Parallax Error Avoidance

With x-ray radiation, the avoidance of parallax error is not as intuitive as it is the case with visible light radiation, due to the fact that x-rays excite fluorescence throughout the whole volume of the phosphorescent material. Beam visualization that is not along the x-ray beam requires significant effort to identify from which depth the fluorescence radiation is emanating, in order to ascertain the center of intensity, and beam shape. Phosphor pads have varying density and a rough surface, which lead to inaccurate information about the x-ray beam shape and location. On-axis view along x-ray beam eliminates parallax error. When using on-axis visualization, the surface of the $PbWO_4$ ("PWO") scintillator crystal that is commonly used does not have to be perpendicular to the beam. When the scintillator is rotated 20° degrees with respect to the beam, the primary image of the beam is the same shape and size as the normal incidence image. This is in stark contrast to off-axis visualization, where the observed beam would move when the scintillator distance is changed along the beam, and a beam's perceived shape would change drastically with rotation of the scintillator.

All current crystal centering methods are indirect and comprise two steps. The location of the x-ray beam is determined by having the beam strike a phosphor screen and a fiducially marked cross-hair is placed at the beam location. Then, with the help of a visible light microscope, the target crystal is placed manually at the cross-hairs. Visible illumination is typically done from the side or behind the crystal (bright field illumination).

UV Fluorescence
One Step Detail

The direct imaging method comprises the use of a synchrotron x-ray beam exciting near UV fluorescence that is imaged by the camera. This directly ascertains the location of the crystal with respect to the synchrotron beam. For x-ray excited UV fluorescence the present invention provides two one-step direct methods.

1. Crystal location technique—In instances where the x-ray is larger than the crystal, the crystal glows upon irradiation, revealing its location.—This provides a direct method for finding the crystal location relative to the x-ray beam location.

2. Mini-beam location: In instances where the beam is smaller than the crystal, one knows which spot of the crystal is illuminated by the x-ray beam (i.e. x-ray mini-beam or micro-beam) and from which spot the diffraction originates.

UV Fluorescence
Two Step Detail

UV fluorescence also provides an indirect crystal location/detection technique (done in two steps).

First, the beam location is found using phosphor/scintillator, and information about beam location/size is transferred to video cross-hair overlay system.

In the second step the location of the crystal is found by UV fluorescence, and crystal is moved to the position of the x-ray beam found in step one.

In the indirect imaging method UV excitation is provided by sources such as a 280 nm LED, or a long pulse UV laser such as the 224 nm Ag laser, or the CW DCSS 266 nm laser (Klastech Verve) or similar far UV sources. Imaging of de-excitation fluorescence allows finding the size, shape, center of optical mass of each of the crystals in the x-ray beam. The only difference between the direct method and the indirect one is the use of the x-ray beam in the direct method.

X-ray and Mid-UV excited UV fluorescence Detail for Biological Samples.

The method described above can be used in a system for x-ray and UV fluorescence automatic alignment of biological crystals in an x-ray beam.

X-ray and UV radiation can excite fluorescence emissions that can be imaged with a CCD type camera. For biological crystals, the de-excitation fluorescence radiation is primarily in the "near" UV range, 300 nm-360 nm. Current research emphasizes crystal visualization in the visible range of the spectrum (400 nm-600 nm).

UV fluorescence in biological crystals originates from the presence of aromatic ring amino acids such as tryptophan, tyrosine, and phenylalanine. There is increased absorption for specific UV wavelengths in each of these materials: e.g. at 280 nm and near 220 nm for tryptophan, and biological materials containing tryptophan show significant UV fluorescence. Introduction of Selenium or other high atomic number elements (e.g. Br or Xe) in the material enhances fluorescence.

The invented system contains hardware and software utilizing x-ray and UV excited fluorescence for centering biological and other crystals, and for non-crystalline materials as well. The system comprises a biological sample, a reflecting microscope, a CCD camera, and the imaging and motion software described above. The invention includes a direct method and an indirect method.

Visible illumination is typically done from the side or behind the crystal (bright field illumination).

FIG. 3 is a block diagram showing the experimental arrangement for UV fluorescence studies. MUV designates Middle Ultraviolet (200 nm-300 nm) radiation and NUV designates Near Ultraviolet (300-400 nm). The block diagram reflects the actual relative location of the several components.

For localization and the visualization of UV fluorescence the Andor iXon 885 EMCCD (Electron Multiplying CCD camera), with a TI chip, was used most successfully.

The invented on-axis visualization solution exploits the fact that paraxial rays are not used in image formation for some reflective optics designs. Exploiting that property, a hole was drilled in a 45° mirror that allows unobstructed transmission of x-rays in that unused paraxial ray space. The invented on-axis visualization method is a significant improvement over other existing designs and over off-axis visualization because it allows beam and sample visualization during data collection, without image degradation, while accommodating all necessary existing instruments. The on-axis solution demonstrated here allows x-ray beam visualization and biological crystal visualization during data collection, with high special resolution, from the x-ray source viewpoint, without image degradation, and with a long working distance. There is no degradation of image quality on the optical axis despite the use of a fairly large hole in 45° mirror for x-ray transport. The parameters of the 45° mirror are determined as a function of the working distance, sample size, and sample to mirror distance. On-axis visualization (along x-ray beam view) simplifies sample and x-ray beam alignment, and eliminates parallax error. Beam centering is significantly easier using on-axis visualization.

Our on-axis visualization using reflective optics utilizing Maksutov-Cassagrain design or any similar objective optics will work for many applications. Among alternative objective designs that could be used are a Newtonian reflector, and a Schmidt-Cassegrain design, There are many possible applications of our on-axis visualization, not limited to samples at synchrotron beams, or x-ray beam visualization, but this design can be used for visualization with any particle beams (e.g. neutrons or lasers) applications.

In operation, a sample is first harvested from a cryogenic bath, and placed in a slip stream of cold fluid so as to be positioned in the path of a radiation beam. This first step assures the native form of the crystal and eliminates any thermal degradation which otherwise would occur prior to imaging of the sample. The thermally-preserved sample is contacted with a radiation beam which first passes through the back side of an externally reflective mirror. Lighting up of the sample, via fluorescence or other means, is reflected by the front surface (i.e. reflective surface of the mirror to a microscope or plurality of microscopes for magnification. The magnified image is captured by a camera and analyzed via standard crystallography protocol.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the invention without departing from its scope. While the dimensions and types of materials described herein are intended to define the parameters of the invention, they are by no means limiting, but are instead are exemplary embodiments. Many other embodiments will be apparent to those of skill in the art upon reviewing the above description. The scope of the invention should, therefore, be determined with reference to the appended claims, along with the full scope of equivalents to which such claims are entitled. In the appended claims, the terms "including" and "in which" are used as the plain-English equivalents of the terms "comprising" and "wherein." Moreover, in the following claims, the terms "first," "second," and "third," are used merely as labels, and are not intended to impose numerical requirements on their objects. Further, the limitations of the following claims are not written in means-plus-function format and are not intended to be interpreted based on 35 U.S.C. §112, sixth paragraph, unless and until such claim limitations expressly use the phrase "means for" followed by a statement of function void of further structure.

The invention claimed is:

1. A method for on-axis visualization of a target sample placed in an x-ray beam, said method comprising:
   a) placing the sample in the path of the x-ray beam;
   b) positioning a mirror, having an external reflective surface such that said surface faces the sample to facilitate viewing of photons traveling towards the x-ray beam;
   c) collecting photons emanating from said sample that have been reflected by said mirror with a reflecting microscope;
   d) counting and analyzing photons collected by said microscope with a camera; and
   d) storing and analyzing data collected by the camera.

2. The method as recited in claim 1 wherein regions of the mirror define a passage extending transversely through the mirror at a 45 degree angle to said reflecting surface to allow said x-ray photon beam to traverse said mirror through said passage before said beam strikes the sample.

3. The method as recited in claim 1 wherein the reflecting microscope is selected to be of the Matsukov-Cassegrain type.

4. The method as recited in claim 1 further comprising illuminating said sample with UV radiation capable of exciting the emission of fluorescent radiation.

5. The method as recited in claim 1 wherein an xyz stage positions said sample around three independent pre-determined axes and selecting locations for said sample, mirror, and microscope to allow these positions.

6. The method as recited in claim 5 wherein said positions constitute a set of positions along the Euler angles of the sample.

7. The method as recited in claim 1 further comprising contacting the sample with a continuous stream of gas chosen from the group consisting of liquid nitrogen, liquid helium and combinations thereof.

8. The method as recited in claim 1 wherein said camera is a CCD camera.

9. The method as recited in claim 1 wherein said camera is an EM-CCD camera.

10. An apparatus for on-axis visualization of a target sample placed in a photon beam, the apparatus comprising:
    a) a mirror with an external reflecting surface facing the sample, said mirror in close spatial relationship to the sample;
    b) a reflecting microscope placed so as to collect photons emanating from the sample that have been reflected by said mirror;
    c) a camera suitable for counting and analyzing photons collected by said microscope; and
    d) means for storing and analyzing data collected by the camera.

11. The apparatus as recited in claim 10 further comprising:
    a passage bored through the mirror at a 45 degree angle to said reflecting surface such
    that the photon beam traverses said mirror through said passage before the beam strikes the sample.

12. The apparatus as recited in claim 10 wherein the reflecting microscope is selected to be of the Matsukov-Cassegrain type.

13. The apparatus as recited in claim 10 further comprising a photo source illuminating said sample with UV radiation capable of exciting the emission of fluorescent radiation.

14. The apparatus as recited in claim 10 further comprising an xyz stage for positioning said sample around three independent pre-determined axes.

15. The apparatus as recited in claim 10 wherein said camera uses a light image intensifier.

16. The apparatus as recited in claim 10 wherein said camera is a CCD camera.

17. The apparatus as recited in claim 10 wherein said camera is an EM-CCD camera.

18. The method as recited in claim 1 wherein said photons emanating from the sample are selected from the group comprising infra-red, visible, and ultra-violet radiation.

19. The apparatus as recited in claim 10 wherein said photons emanating from the sample are selected from the group comprising infra-red, visible, and ultra-violet radiation.

* * * * *

UNITED STATES PATENT AND TRADEMARK OFFICE
CERTIFICATE OF CORRECTION

PATENT NO. : 8,440,986 B2
APPLICATION NO. : 12/766275
DATED : May 14, 2013
INVENTOR(S) : Kazimierz J Gofron et al.

It is certified that error appears in the above-identified patent and that said Letters Patent is hereby corrected as shown below:

In the Specification:

On column 11, line 57, delete "d)" and replace with "e)".

On column 11, line 61, delete the word "photon".

In the Claims:

On column 12, line 43, replace the word "photo" with "photon".

Signed and Sealed this
Eighth Day of October, 2013

Teresa Stanek Rea
*Deputy Director of the United States Patent and Trademark Office*